United States Patent
Whayne (10) Patent No.: US 9,603,657 B2
(45) Date of Patent: *Mar. 28, 2017

(54) VACUUM COAGULATION PROBE FOR ATRIAL FIBRILLATION TREATMENT

(75) Inventor: James G. Whayne, Chapel Hill, NC (US)

(73) Assignee: Atricure, Inc., Mason, OH (US)

(*) Notice: Subject to any disclaimer, the term of this patent is extended or adjusted under 35 U.S.C. 154(b) by 1153 days.

This patent is subject to a terminal disclaimer.

(21) Appl. No.: 12/135,010

(22) Filed: Jun. 6, 2008

(65) Prior Publication Data
US 2008/0243119 A1   Oct. 2, 2008

Related U.S. Application Data (63) Continuation of application No. 11/096,205, filed on Mar. 30, 2005, now Pat. No. 7,410,487, which is a
(Continued)

(51) Int. Cl.
| A61B 18/18 | (2006.01) |
| A61B 18/14 | (2006.01) |
| A61B 18/00 | (2006.01) |

(52) U.S. Cl.
CPC ..... *A61B 18/1492* (2013.01); *A61B 2018/00029* (2013.01); *A61B 2018/00291* (2013.01);
(Continued)

(58) Field of Classification Search
CPC ..... A61B 18/1492; A61B 18/04; A61B 18/08; A61B 18/082; A61B 18/10; A61B 18/085;
(Continued)

(56) References Cited

U.S. PATENT DOCUMENTS

| 4,993,412 A | 2/1991 | Chutorian |
| 5,125,928 A | 6/1992 | Parins et al. |

(Continued)

FOREIGN PATENT DOCUMENTS

| EP | 1518507 | 3/2005 |
| JP | 2005512668 A | 5/2005 |

(Continued)

OTHER PUBLICATIONS

U.S. Appl. No. 11/558,423, filed Nov. 9, 2006 in the name of Whayne et al., final Office Action mailed Apr. 27, 2010.
(Continued)

*Primary Examiner* — Michael Peffley
*Assistant Examiner* — Amanda Zink
(74) *Attorney, Agent, or Firm* — Levine Bagade Han LLP (57) ABSTRACT

An embodiment of the invention includes a surgical device for coagulating soil tissue such as atrial tissue in the treatment of atrial fibrillation, atrial flutter, and atrial tachycardia. The surgical device can include at least one elongate member comprising conductive elements adapted to coagulate soft tissue when radiofrequency or direct current energy is transmitted to the conductive elements. Openings through said conductive elements are routed through lumens in the elongate member to a vacuum source to actively engage the soft tissue surface intended to coagulate into intimate contact with the conductive elements to facilitate the coagulation process and ensure the lesions created are consistent, contiguous, and transmural. The embodiments of the invention can also incorporate cooling openings positioned near the conductive elements and coupled with a vacuum source or an injection source to transport fluid though the cooling openings causing the soft tissue surface to cool thus pushing the maximum temperature deeper into tissue. The embodiments of the invention can also incorporate features to
(Continued)

tunnel between anatomic structures or dissect around the desired tissue surface to coagulate thereby enabling less invasive positioning of the soft tissue coagulating device and ensuring reliable and consistent heating of the soft tissue.

11 Claims, 10 Drawing Sheets

Related U.S. Application Data continuation of application No. 10/172,296, filed on Jun. 14, 2002, now Pat. No. 6,893,442.

(52) U.S. Cl.
CPC .............. *A61B 2018/00351* (2013.01); *A61B 2218/002* (2013.01); *A61B 2218/007* (2013.01)

(58) Field of Classification Search
CPC ... A61B 18/1206; A61B 18/14; A61B 18/148; A61B 18/149; A61B 2018/00029; A61B 2018/00291; A61B 2018/00351; A61B 2218/002; A61B 2218/007
USPC .......................................................... 606/49
See application file for complete search history.

(56) References Cited

U.S. PATENT DOCUMENTS

| | | | |
|---|---|---|---|
| 5,277,696 A | 1/1994 | Hagen | |
| 5,322,064 A | 6/1994 | Lundquist | |
| 5,366,490 A | 11/1994 | Edwards et al. | |
| 5,562,722 A | 10/1996 | Racz et al. | |
| 5,571,088 A | 11/1996 | Lennox et al. | |
| 5,725,523 A | 3/1998 | Mueller | |
| 5,733,280 A | 3/1998 | Avitall | |
| 5,769,847 A | 6/1998 | Panescu et al. | |
| 5,782,760 A | 7/1998 | Schaer | |
| 5,782,828 A | 7/1998 | Chen et al. | |
| 5,785,706 A | 7/1998 | Bednarek | |
| 5,788,681 A | 8/1998 | Weaver et al. | |
| 5,836,311 A | 11/1998 | Borst et al. | |
| 5,851,206 A | 12/1998 | Guglielmi et al. | |
| 5,885,278 A * | 3/1999 | Fleischman | 606/41 |
| 5,919,188 A | 7/1999 | Shearon et al. | |
| 5,957,882 A | 9/1999 | Nita et al. | |
| 5,971,983 A | 10/1999 | Lesh | |
| 6,063,081 A | 5/2000 | Mulier et al. | |
| 6,071,279 A | 6/2000 | Whayne et al. | |
| 6,071,281 A | 6/2000 | Burnside et al. | |
| 6,080,151 A | 6/2000 | Swartz et al. | |
| 6,086,583 A | 7/2000 | Ouchi | |
| 6,120,500 A | 9/2000 | Bednarek et al. | |
| 6,161,543 A * | 12/2000 | Cox et al. | 128/898 |
| 6,190,382 B1 | 2/2001 | Ormsby et al. | |
| 6,210,408 B1 | 4/2001 | Chandrasekaran et al. | |
| 6,237,555 B1 | 5/2001 | Dykstra et al. | |
| 6,237,605 B1 * | 5/2001 | Vaska et al. | 128/898 |
| 6,237,606 B1 | 5/2001 | Zikorus et al. | |
| 6,245,062 B1 | 6/2001 | Berube et al. | |
| 6,264,650 B1 | 7/2001 | Hovda et al. | |
| 6,264,654 B1 | 7/2001 | Swartz et al. | |
| 6,296,638 B1 | 10/2001 | Davison et al. | |
| 6,305,378 B1 | 10/2001 | Lesh | |
| 6,311,692 B1 | 11/2001 | Vaska et al. | |
| 6,314,916 B1 | 11/2001 | Watson, Sr. | |
| 6,314,962 B1 | 11/2001 | Vaska et al. | |
| 6,314,963 B1 | 11/2001 | Vaska et al. | |
| 6,325,798 B1 | 12/2001 | Edwards et al. | |
| 6,364,876 B1 | 4/2002 | Erb et al. | |
| 6,425,895 B1 | 7/2002 | Swanson et al. | |
| 6,463,223 B1 | 10/2002 | Karakama et al. | |
| 6,463,332 B1 | 10/2002 | Aldrich | |
| 6,464,699 B1 | 10/2002 | Swanson | |
| 6,474,340 B1 | 11/2002 | Vaska et al. | |
| 6,482,202 B1 | 11/2002 | Goble et al. | |
| 6,484,727 B1 | 11/2002 | Vaska et al. | |
| 6,500,141 B1 * | 12/2002 | Irion et al. | 604/22 |
| 6,506,180 B1 | 1/2003 | Lary | |
| 6,514,250 B1 | 2/2003 | Jahns et al. | |
| 6,522,930 B1 | 2/2003 | Schaer et al. | |
| 6,529,778 B2 | 3/2003 | Prutchi | |
| 6,558,382 B2 | 5/2003 | Jahns et al. | |
| 6,579,288 B1 | 6/2003 | Swanson et al. | |
| 6,605,087 B2 | 8/2003 | Swartz et al. | |
| 6,645,200 B1 | 11/2003 | Koblish et al. | |
| 6,645,202 B1 | 11/2003 | Pless et al. | |
| 6,652,518 B2 | 11/2003 | Wellman et al. | |
| 6,663,622 B1 | 12/2003 | Foley et al. | |
| 6,689,128 B2 | 2/2004 | Sliwa, Jr. et al. | |
| 6,701,931 B2 | 3/2004 | Sliwa, Jr. et al. | |
| 6,719,755 B2 | 4/2004 | Sliwa, Jr. et al. | |
| 6,726,684 B1 | 4/2004 | Woloszko et al. | |
| 6,764,487 B2 | 7/2004 | Mulier et al. | |
| 6,849,075 B2 | 2/2005 | Bertolero et al. | |
| 6,887,238 B2 | 5/2005 | Jahns et al. | |
| 6,887,249 B1 | 5/2005 | Houser et al. | |
| 6,893,442 B2 * | 5/2005 | Whayne | 606/49 |
| 6,917,834 B2 | 7/2005 | Koblish et al. | |
| 6,918,908 B2 | 7/2005 | Bonner et al. | |
| 6,949,095 B2 | 9/2005 | Vaska et al. | |
| 7,033,352 B1 | 4/2006 | Gauthier et al. | |
| 7,052,491 B2 | 5/2006 | Erb et al. | |
| 7,063,698 B2 | 6/2006 | Whayne et al. | |
| 7,115,126 B2 | 10/2006 | Berube et al. | |
| 7,144,363 B2 | 12/2006 | Pai et al. | |
| 7,207,988 B2 | 4/2007 | Leckrone et al. | |
| 7,226,448 B2 | 6/2007 | Bertolero et al. | |
| 7,371,233 B2 | 5/2008 | Swanson et al. | |
| 7,387,627 B2 | 6/2008 | Erb et al. | |
| 7,399,300 B2 | 7/2008 | Bertolero et al. | |
| 7,410,487 B2 | 8/2008 | Whayne | |
| 7,572,257 B2 | 8/2009 | Whayne et al. | |
| 7,758,578 B2 | 7/2010 | Whayne et al. | |
| 7,780,661 B2 | 8/2010 | Whayne et al. | |
| 7,803,155 B2 | 9/2010 | Whayne et al. | |
| 8,034,053 B2 | 10/2011 | Whayne et al. | |
| 8,454,598 B2 | 6/2013 | Whayne et al. | |
| 2001/0025175 A1 | 9/2001 | Panescu et al. | |
| 2001/0029349 A1 | 10/2001 | Leschinsky | |
| 2002/0002372 A1 * | 1/2002 | Jahns et al. | 606/41 |
| 2002/0045895 A1 | 4/2002 | Sliwa et al. | |
| 2002/0072739 A1 | 6/2002 | Lee et al. | |
| 2002/0072741 A1 | 6/2002 | Sliwa et al. | |
| 2002/0091299 A1 | 7/2002 | Silverman et al. | |
| 2002/0095139 A1 | 7/2002 | Keogh et al. | |
| 2002/0111608 A1 | 8/2002 | Baerveldt et al. | |
| 2002/0133150 A1 | 9/2002 | Whayne et al. | |
| 2002/0138109 A1 | 9/2002 | Keogh et al. | |
| 2002/0193851 A1 | 12/2002 | Silverman et al. | |
| 2003/0036754 A1 * | 2/2003 | Erb et al. | 606/33 |
| 2003/0109874 A1 | 6/2003 | Dennis | |
| 2003/0114844 A1 | 6/2003 | Ormsby et al. | |
| 2003/0233090 A1 | 12/2003 | Whayne | |
| 2003/0233091 A1 | 12/2003 | Whayne et al. | |
| 2004/0019349 A1 | 1/2004 | Fuimaono et al. | |
| 2004/0153057 A1 | 8/2004 | Davison et al. | |
| 2004/0186467 A1 | 9/2004 | Swanson et al. | |
| 2004/0220657 A1 | 11/2004 | Nieminen et al. | |
| 2005/0004516 A1 | 1/2005 | Vanney | |
| 2005/0045895 A1 | 3/2005 | Emerson et al. | |
| 2005/0119545 A1 | 6/2005 | Swanson | |
| 2005/0149152 A1 | 7/2005 | Bertolero et al. | |
| 2005/0240175 A1 | 10/2005 | Bertolero et al. | |
| 2005/0288666 A1 | 12/2005 | Bertolero et al. | |
| 2006/0004388 A1 | 1/2006 | Whayne et al. | |
| 2006/0009762 A1 | 1/2006 | Whayne | |
| 2006/0015165 A1 | 1/2006 | Bertolero et al. | |
| 2006/0122680 A1 | 6/2006 | Auth et al. | |
| 2006/0184167 A1 | 8/2006 | Vaska et al. | |
| 2006/0200124 A1 | 9/2006 | Whayne et al. | |
| 2006/0206113 A1 | 9/2006 | Whayne et al. | |
| 2006/0235381 A1 | 10/2006 | Whayne et al. | |

(56) References Cited

U.S. PATENT DOCUMENTS

| | | |
|---|---|---|
| 2006/0293646 A1 | 12/2006 | Whayne et al. |
| 2007/0005051 A1 | 1/2007 | Kampa |
| 2007/0043351 A1 | 2/2007 | Fleischman et al. |
| 2007/0083082 A1 | 4/2007 | Kiser et al. |
| 2007/0083225 A1 | 4/2007 | Kiser et al. |
| 2007/0156185 A1 | 7/2007 | Swanson et al. |
| 2007/0239155 A1 | 10/2007 | Ibrahim et al. |
| 2007/0249991 A1 | 10/2007 | Whayne et al. |
| 2007/0250058 A1 | 10/2007 | Whayne et al. |
| 2008/0114342 A1 | 5/2008 | Whayne et al. |
| 2008/0114354 A1 | 5/2008 | Whayne et al. |
| 2008/0114355 A1 | 5/2008 | Whayne et al. |
| 2009/0254009 A1 | 10/2009 | Whayne et al. |
| 2010/0262138 A1 | 10/2010 | Whayne et al. |
| 2011/0137311 A1 | 6/2011 | Whayne et al. |
| 2011/0282344 A1 | 11/2011 | Whayne et al. |
| 2013/0018370 A1 | 1/2013 | Whayne et al. |

FOREIGN PATENT DOCUMENTS

| | | |
|---|---|---|
| WO | WO 01/58373 | 8/2001 |
| WO | WO 01/80755 | 11/2001 |
| WO | WO 03/053259 | 7/2003 |
| WO | WO 2004/028233 | 6/2004 |
| WO | WO 2004/093698 | 11/2004 |
| WO | WO 2005/046456 | 5/2005 |
| WO | WO 2006/009856 | 1/2006 |

OTHER PUBLICATIONS

U.S. Appl. No. 11/408,302, filed Apr. 21, 2006 in the name of Fleischman et al., non-final Office Action mailed Nov. 3, 2009.
U.S. Appl. No. 11/558,420, filed Nov. 9, 2006 in the name of Whayne et al., non-final Office Action mailed May 12, 2010.
U.S. Appl. No. 11/432,962, filed May 12, 2006 in the name of Whayne, Non-final Office Action mailed Apr. 21, 2010.
U.S. Appl. No. 11/419,840, filed May 23, 2006 in the name of Whayne, final Office Action mailed Apr. 21, 2010.
International Patent Application No. PCT/US2006/015009 in the name of Fleischman et al. filed Apr. 21, 2006, International Search Report and Written Opinion mailed Sep. 27, 2006.
International Patent Application No. PCT/US2006/060753 in the name of Whayne et al. filed Nov. 9, 2006, International Search Report and Written Opinion mailed Dec. 3, 2007.
U.S. Appl. No. 10/172,296, filed Jun. 14, 2002 in the name of Whayne, Non-final Office Action mailed Oct. 17, 2003.
U.S. Appl. No. 10/172,296, filed Jun. 14, 2002 in the name of Whayne, Notice of Allowance mailed Jul. 23, 2004.
U.S. Appl. No. 10/425,251, filed Apr. 29, 2003 in the name of Whayne, Final Office Action mailed Nov. 14, 2005.
U.S. Appl. No. 10/425,251, filed Apr. 29, 2003 in the name of Whayne, Non-final Office Action mailed Jan. 20, 2006.
U.S. Appl. No. 10/425,251, filed Apr. 29, 2003 in the name of Whayne, Non-final Office Action mailed May 25, 2005.
U.S. Appl. No. 10/425,251, filed Apr. 29, 2003 in the name of Whayne, Notice of Allowance mailed Apr. 12, 2006.
U.S. Appl. No. 11/096,205, filed Mar. 30, 2005 in the name of Whayne, Non-final Office Action mailed Sep. 19, 2007.
U.S. Appl. No. 11/096,205, filed Mar. 30, 2005 in the name of Whayne, Notice of Allowance mailed May 1, 2008.
U.S. Appl. No. 11/208,465, filed Aug. 18, 2008 in the name of Whayne et al., Final Office Action mailed Jan. 7, 2009.
U.S. Appl. No. 11/208,465, filed Aug. 18, 2008 in the name of Whayne et al., Non-final Office Action mailed Jul. 29, 2008.
U.S. Appl. No. 11/208,465, filed Aug. 18, 2008 in the name of Whayne et al., Notice of Allowance mailed Jun. 11, 2009.
U.S. Appl. No. 11/419,840, filed May 23, 2006 in the name of Whayne, Non-final Office Action mailed Aug. 31, 2009.
U.S. Appl. No. 11/432,962, filed May 12, 2006 in the name of Whayne, Non-final Office Action mailed Sep. 1, 2009.
U.S. Appl. No. 11/433,248, filed May 12, 2006 in the name of Whayne, Non-final Office Action mailed Jan. 5, 2009.
U.S. Appl. No. 11/433,248, filed May 12, 2006 in the name of Whayne, Non-final Office Action mailed Sep. 3, 2009.
U.S. Appl. No. 11/558,423, filed Nov. 9, 2006 in the name of Whayne et al., Non-final Office Action mailed Aug. 19, 2009.
European Patent Application No. 06751099.0 filed Apr. 21, 2006 in the name of Kiser et al., Supplementary European Search Report and European Search Opinion mailed Sep. 3, 2009.
European Patent Application No. 06751099.0 filed Apr. 21, 2006 in the name of Kiser et al., office action mailed Nov. 16, 2009.
International Patent Application No. PCT/US2006/015268 filed Apr. 21, 2006 in the name of Kiser et al., International Search Report and Written Opinion mailed Oct. 3, 2007.
International Patent Application No. PCT/US2006/060749 in the name of Whayne et al. filed Nov. 9, 2006, International Search Report and Written Opinion mailed Nov. 21, 2007.
International Patent Application No. PCT/US2009/040981 in the name of Sicvol filed Apr. 17, 2009, International Search Report and Written Opinion mailed Jun. 11, 2009.
International Patent Application No. PCT/US2009/046780 in the name of Whayne et al. filed Jun. 9, 2009, International Search Report and Written Opinion mailed Jul. 28, 2009.
U.S. Appl. No. 11/155,305, filed Jun. 17, 2005 in the name of Whayne et al., Final Office Action mailed Aug. 13, 2009.
U.S. Appl. No. 11/155,305, filed Jun. 17, 2005 in the name of Whayne et al., Non-final Office Action mailed Oct. 28, 2008.
U.S. Appl. No. 11/155,338, filed Jun. 17, 2005 in the name of Whayne et al., Final Office Action mailed Dec. 8, 2009.
U.S. Appl. No. 11/155,338, filed Jun. 17, 2005 in the name of Whayne et al., Non-final Office Action mailed Feb. 17, 2009.
U.S. Appl. No. 11/408,302, filed Apr. 21, 2006 in the name of Fleischman, Non-final Office Action mailed Nov. 3, 2009.
U.S. Appl. No. 11/408,307, filed Apr. 21, 2006 in the name of Kiser at al., Non-final Office Action mailed Sep. 17, 2009.
U.S. Appl. No. 11/408,315, filed Apr. 21, 2006 in the name of Kiser et al., Non-final Office Action mailed Sep. 22, 2009.
U.S. Appl. No. 11/419,840, filed May 23, 2006 in the name of Whayne, Non-final Office Action mailed Dec. 3, 2008.
U.S. Appl. No. 11/432,962, filed May 12, 2006 in the name of Whayne, Non-final Office Action mailed Dec. 3, 2008.
U.S. Appl. No. 11/433,248, filed May 12, 2006 in the name of Whayne, Notice of Allowance mailed Jun. 16, 2010.
U.S. Appl. No. 11/433,248, filed May 12, 2006 in the name of Whayne, Notice of Allowance mailed May 27, 2010.
Cragg, et al., "Endovascular diathermic vessel occlusion," *Radiology*, 144:303-308, 1982.
Gorisch et al., "Heat-induced contraction of blood vessels," *Lasers in Surgery and Medicine*, 2:1-13, 1982.
Nath, et al., "Cellular electrophysiologic effects of hyperthennia on isolated guinea pig papillary muscle: implications for catheter ablation," *Circulation*, 88:1826-1831, 1993.

* cited by examiner

VACUUM COAGULATION PROBE FOR ATRIAL FIBRILLATION TREATMENT

CROSS-REFERENCE TO RELATED APPLICATIONS

This application is a continuation of U.S. application Ser. No. 11/096,205 filed Mar. 30, 2005, now U.S. Pat. No. 7,410,487 issued Aug. 12, 2008, which is a continuation of U.S. application Ser. No. 10/172,296 filed Jun. 14, 2002, now U.S. Pat. No. 6,893,442 issued May 17, 2005, the contents of which are incorporated herein by reference in its entirety.

FIELD OF THE INVENTIONS

Embodiments of the invention relate to devices and methods for less invasive treatment of atrial fibrillation. More particularly, certain embodiments of the invention relate to ablation and/or coagulation probes that utilize suction to ensure consistent and intimate tissue contact. These vacuum-assisted coagulation probes are capable of creating transmural, curvilinear lesions capable of preventing the propagation of wavelets that initiate and sustain atrial fibrillation, atrial flutter, or other arrhythmia substrate. The vacuum-assisted coagulation probes facilitate less invasive surgery involving thorascopic access and visualization to the target coagulation sites. Additionally, the vacuum-assisted coagulation probes of the invention are suitable for coagulating soft tissues (e.g. of the atria to treat atrial fibrillation, atrial flutter, or other arrhythmia) through a median sternotomy, lateral thoracotomy, intercostals port-access, mini-sternotomies, other less invasive approaches involving Xiphoid access, inguinal approaches, or sub-thoracic approaches adjacent the diaphragm. Alternatively, the vacuum-assisted coagulation probes can be modified for catheter-based applications by elongating the shaft and altering the diameters and other feature dimensions for intravascular access.

The vacuum-assisted coagulation probes can also be used to coagulate other soft tissues for cancer therapy in a wide-variety of applications (e.g. liver, prostate, colon, esophageal, gastrointestinal, gynecological, etc.), or shrinking of collagen in tissue structures such as skin, tendons, muscles, ligaments, vascular tissue during arthroscopic, laparoscopic, or other minimally invasive procedures.

Certain embodiments of devices and methods of the invention also enable tunneling though and/or dissecting soft tissue structures by injecting fluid (air, $CO_2$, saline, etc.) in high intensity streams that separate tissue structures by disrupting fatty deposits, ligaments, adventitial tissue, or other structure that holds anatomic structures together without damaging the anatomic structure the device is dissecting free or otherwise exposing. These devices of the invention enable less invasive access without having to manually dissect tissue structures to place the vacuum-assisted coagulation probes. As such, these fluid dissecting devices are capable of tunneling through the pulmonary veins, separate the pulmonary veins, the aorta, the pulmonary artery, and other anatomy from the atria to provide a path for the vacuum-assisted coagulation probe to directly appose the atrial epicardium throughout the desired length the lesion is expected to span, which is required to create transmural, curvilinear lesions. These embodiments may alternatively dissect other soft tissue structures during applications such as endoscopic saphenous vein harvesting, left internal mammary artery dissection, etc.

DESCRIPTION OF THE RELATED ART

Atrial fibrillation surgery involving radiofrequency, d.c., microwave, or other thermal ablation of atrial tissue has a limitation in that tissue contact throughout the length of the electrode(s) is/are not consistent causing variability in the transmission of energy throughout the target length of ablated/coagulated tissue. This produces gaps of viable tissue that promote propagation of wavelets that sustain atrial fibrillation, or produce atrial flutter, atrial tachycardia, or other arrhythmia substrate. Another influence in the inability of existing thermal ablation probes to create complete curvilinear, transmural lesions is the presence of convective cooling on the opposite surface of the atrium producing a heat sink that decreases the maximum temperature at this surface hereby preventing the lesions from consistently extending transmural through the entire wall of the atrium. This is especially relevant during beating-heart therapies in which the coagulation/ablation probe is placed against the epicardial surface, and blood flowing along the endocardium removes heat thus producing a larger gradient between temperature immediately under the probe electrodes along the epicardium and that at the endocardium. Increased tissue contact is capable of reversing this effect by evoking a compression of the tissue that shortens the wall thickness of the atria, ensuring consistent contact throughout the length of the electrode(s), and increasing the efficiency of thermal conduction from the endocardium. As such a more consistent and reliable lesion is created.

BRIEF DESCRIPTION OF DRAWINGS

Several exemplary embodiments of the present invention, and many features and advantages of those exemplary embodiments will be elaborated in the following detailed description and accompanying drawings, in which:

FIGS. 2c and 2d show sectional views taken along B-B and C-C of FIG. 2a;

DETAILED DESCRIPTION

A need exists for vacuum coagulation probe devices and methods that create contiguous, curvilinear, transmural lesions in the atria to treat atrial fibrillation, atrial fibrillation, or other arrhythmia substrate. In addition, such devices and methods could simplify other soft tissue coagulation procedures by ensuring intimate tissue contact wide precisely and effectively heating a region of soft tissue. The needed technology also could enable certain procedures to be performed less invasive through limited incisions that previously required large, open incisions with inherent morbidity and risks to other anatomic structures. Such inventive devices and methods thus could enable patients to undergo such reparative or therapeutic surgical procedures while enduring less pain, expedited hospital stays, and shorter rehabilitative and recovery times.

The present invention relates to methods and devices that enable reliable and controlled coagulation of soft tissue during less invasive procedures. To accomplish this, the coagulation probe incorporates vacuum conduits associated with the electrode(s) to urge the soft tissue into intimate contact with the edges of the electrode(s) and ensure efficient transmission of energy capable of consistently and completely heating a desired region of soft tissue. The vacuum coagulation probe embodiments of the invention also enable convective cooling of the tissue surface to move the maximum temperature deeper into tissue and create larger and deeper lesions. The vacuum coagulation probe embodiments of the invention can also incorporate tunneling and/or dissecting features capable of introducing the vacuum coagulation probe between anatomic structures around the atria which would otherwise be inaccessible without mechanical dissection, and/or expose a region of atria to produce consistent tissue contact, required to ensure contiguous, transmural lesions.

The following is a detailed description of certain exemplary embodiments of the inventions. This detailed description is not to be taken in a limiting sense, but is made merely for the purpose of illustrating certain general principles of the inventions.

This patent application discloses a number of exemplary embodiments, mainly in the context of soft tissue coagulation accomplished though less invasive approaches (e.g. thoracoscopic, arthroscopic, laparoscopic, percutaneous, or other minimally invasive procedures). The vacuum coagulation probe embodiments disclosed herein can produce intimate contact between a soft tissue surface and electrode(s) used to transmit energy capable of heating the soft tissue until irreversible injury is achieved making the soft tissue non-viable and unable to propagate electrical impulses, mutate, reproduce or other unwanted function. The vacuum coagulation probe embodiments also enable supporting and/or repositioning the soft tissue during coagulation to prevent or minimize shrinking or other change in the shape of the soft tissue associated with heat causing the collagen in the soft tissue to denature. The vacuum coagulation probe embodiments also address issues related to inadequate access to the soft tissue during less invasive approaches by tunneling and/or dissecting the anatomic structures to produce a path to the coagulation sites, and expose the surface of the soft tissue. This capability is especially relevant when coagulating atrial tissue along the posterior region of the heart, characteristic of creating lesions along the left atrial epicardium about the pulmonary veins.

Nevertheless, it should be appreciated that the vacuum coagulation probe devices can be applicable for use in other indications involving devices that are used to coagulate soft tissue, and/or tunnel between or dissect anatomic structures where access to the tissue is limited by a small opening into the cavity, confined space at the soft tissue interface, difficult to reach locations, or other anatomic limitation. The embodiments of the invention can be configured for the human anatomy; however, it should be noted that the embodiments of the invention can, in some cases, be tailored to other species, such as canine, ovine, porcine, bovine, or horses, by changing the geometry and sizes of the structures.

An additional benefit of vacuum coagulation probe devices can involve the ease of deployment and the rapid healing post-procedure. The small incision used to access the soft tissue during such procedures accelerates the healing process and reduces the visible scar. The vacuum coagulation probe devices can be capable of being deployed through a thoracostomy, thoracotomy, median sternotomy, mini-sternotomy, mini-thoracotomy, xiphoid access, subthoracic access, arthroscopic, or laparoscopic approach, thereby potentially eliminating the need for long incisions to access the soft tissue and corresponding anatomic structures.

The vacuum coagulation probe, and corresponding components, can be fabricated from at least one rod, wire, band, bar, tube, sheet, ribbon, other raw material having the desired pattern, cross-sectional profile, and dimensions, or a combination of cross-sections. The rod, wire, band, bar, sheet, tube, ribbon, or other raw material can be fabricated by extruding, injection molding, press-forging, rotary forging, bar rolling, sheet rolling, cold drawing, cold rolling, using multiple cold-working and annealing steps, casting, or otherwise forming into the desired shape. The components of the vacuum coagulation probe may be cut from raw material by conventional abrasive sawing, water jet cutting, laser cutting, ultrasonic cutting, EDM machining, photochemical etching, or other techniques to cut the lumens, pores, ports and/or other features of the vacuum coagulation probe from the raw material. Components of the vacuum coagulation probe can be attached by laser welding, adhesively bonding, ultrasonic welding, radiofrequency welding, soldering, spot welding, or other attachment means.

For several of the vacuum coagulation probe embodiments below, various components can be fabricated from at least one wire, tube, ribbon, sheet, rod, band or bar of raw material cut to the desired configuration and thermally formed into the desired 3-dimensional configuration. When thermally forming (e.g. annealing) components, they can be stressed into the desired resting configuration using mandrels and/or forming fixtures having the desired resting shape of the puncturing component, and heated to between 300 and 600 degrees Celsius for a period of time, typically between 15 seconds and 10 minutes. Alternatively, the components may be heating immediately prior to stressing. Once the volume of material reaches the desired temperature, the component is quenched by inserting into chilled or room temperature water or other fluid, or allowed to return to ambient temperature. As such the components can be fabricated into their resting configuration. When extremely small radii of curvature are desired, multiple thermal forming steps can be utilized to sequentially bend the component into smaller radii of curvature.

When fabricating the vacuum coagulation probe components from tubing, the raw material can have an oval, circular, rectangular, square, trapezoidal, or other cross-sectional geometry capable of being cut into tile desired pattern. After cutting the desired pattern of lumens, ports, and pores, the components can be formed into the desired shape, stressed, heated, for example, between 300° C. and 600° C., and allowed to cool in the preformed geometry to set the shape of the components, as discussed above.

Once the components are fabricated and formed into the desired 3-dimensional geometry, they can be tumbled, sand blasted, bead blasted, chemically etched, ground, mechanically polished, electropolished, or otherwise treated to remove any edges and/or produce a smooth surface.

Holes, slots, notches, other cut-away areas, or regions of ground material can be incorporated in the components to tailor the stiffness profile. Cutting and treating processes described above can be used to fabricate the slots, holes, notches, cut-away regions, and/or ground regions in the desired pattern to taper the stiffness along, focus the stiffness along the length of, reinforce specific regions of, or otherwise customize the stiffness profile of the vacuum probe components.

Figures 1A, 1B, 1C, 1D:
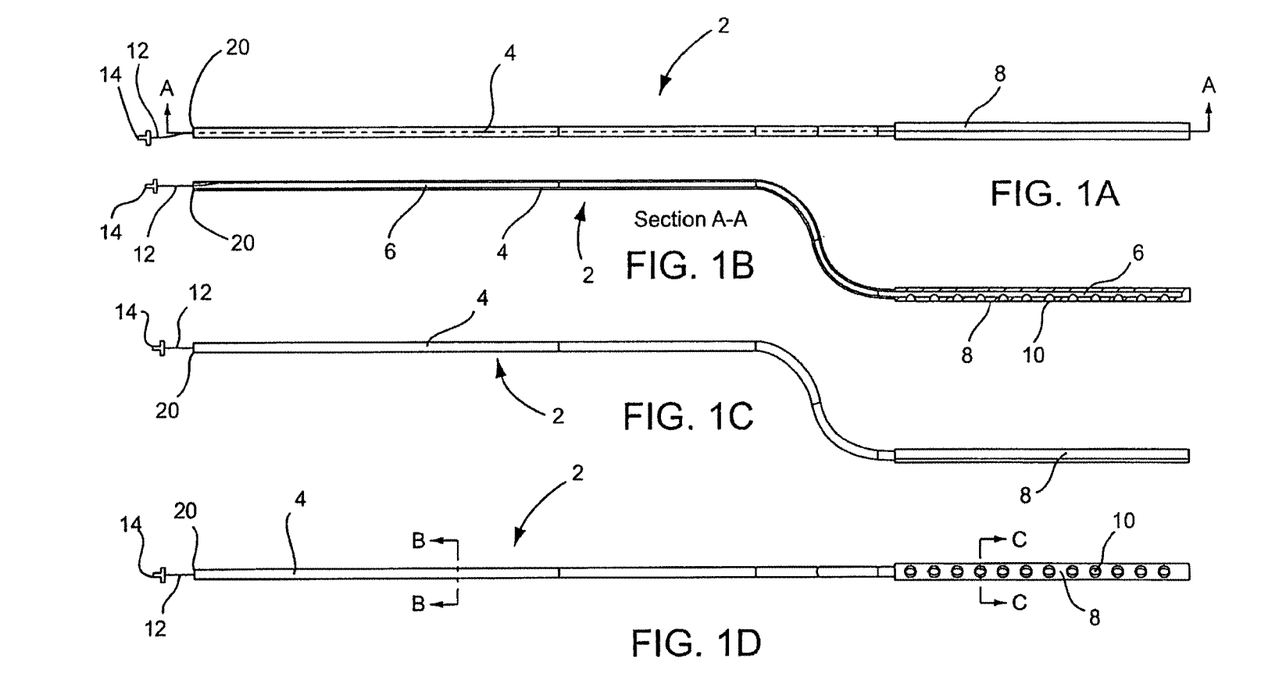
FIGS. 1a to 1d show a top view, a side-sectional view taken along A-A of FIG. 1a, a side view, and a bottom view of a vacuum coagulation probe embodiment of the invention.
Figure 1E:
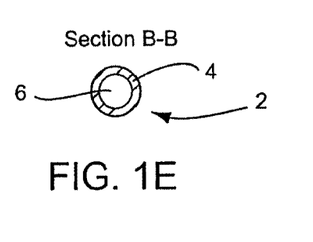
FIGS. 1e and 1f show cross-sectional views taken along B-B and C-C of FIG. 1d.

FIGS. 1a to d show a top view, a side-sectional view taken along A-A, a side view, and a bottom view of a vacuum coagulation probe 2 embodiment of the invention. The vacuum coagulation probe 2 incorporates a shaft 4 that defines a lumen 6, as shown in FIG. 1e. The shaft 4 may be fabricated from a metal (e.g. titanium), metal alloy (e.g. stainless steel, spring steel, nickel titanium) PEBAX®, polyester, polyurethane, urethane, silicone, polyimide, other thermoplastic, thermoset plastic, or elastomer, or braided metallic wires covered with a polymer. The shaft 4 is preferably fabricated from tubing having a diameter between 0.040" and 0.300" and a wall thickness between 0.004" and 0.080" depending on the type of material and stiffness requirements. The tubing may have a circular cross-section, elliptical cross-section, rectangular cross-section, or other geometry depending on the stiffness requirements, access characteristics, and other considerations. The shaft 4 may be fabricated from multi-lumen tubing having two or more lumens serving specific functions. At its proximal end, the shaft 4 is bonded to a handle (not shown) that incorporates a port(s) 20 that feeds the lumen(s) 6. The port(s) 20 may incorporate a luer adaptor(s) or other tubing connection to facilitate attaching IV tubing or other feeding tube capable of connecting to a vacuum source.

The handle (not shown) also houses at least one electrical connector 14 to which wire(s) 12 are attached at the proximal end. The wire(s) 12 are routed to the electrode(s) 8 to enable transmitting energy (radiofrequency, or direct current) to the electrode(s). When transmitting radiofrequency energy in unipolar fashion to a large surface area, reference electrode placed apart from the coagulation electrode, a single wire is routed to each electrode and connected to a radiofrequency generator. When transmitting d.c. or radiofrequency energy in bipolar fashion to electrode pairs, individual wires are connected to each of two or more individual, closely-spaced electrodes. When utilizing resistive heating of the electrode—and relying on conduction to transfer heat to adjacent tissue, two wires are connected to each electrode (e.g. resistive element in this case) spaced apart so the entire length of the electrode heats to the desired temperature and the heat is conducted to contacted tissue.

Temperature sensors (not shown) may be associated with each electrode with wires routed along the shaft to the handle where they are connected to an electrical connector (14) capable of transmitting the temperature signal to a radiofrequency generator with temperature monitoring or control capabilities or a separate temperature monitor. U.S. Pat. No. 5,769,847, entitled "Systems and methods for controlling tissue ablation using multiple temperature sensing elements" and incorporated herein by reference, describes tissue coagulation systems utilizing multiple electrodes and temperature sensor associated with each electrode to controllably transmit radiofrequency energy and maintain all electrode(s) essentially at the same temperature.

The vacuum coagulation probe electrode(s) and associated temperature sensors (not shown) may be connected so such a mechanism to control transmission of radiofrequency energy to each electrode to control the heating of contacted soft tissue.

Figure 1F:
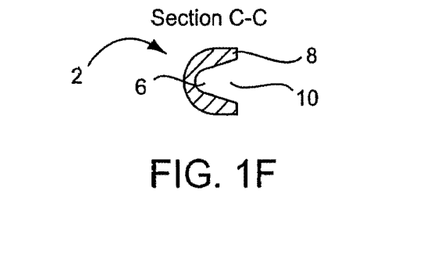

The electrode(s) 8 may be fabricated from one or more lengths of tubing (having a circular, elliptical, rectangular, or other cross-sectional) secured to the shaft 4 at one end and containing a cap at the other end. If more-than one electrode 8 is desired, multiple lengths of tubing may be connected to the shaft 4 separated by short lengths of insulative tubing material. Alternatively, the electrode(s) may be fabricated from wire, having a circular, rectangular, elliptical, or other cross-section, coiled into a helix, interlaced into a mesh or other configuration and placed over and secured to an electrode support. Another electrode configuration includes lengths of sheet or bar material bonded to an electrode support having a semicircular cross-section or other geometry that defines a lumen, with the electrode in place, that is linked to the shaft 4 lumen 6. This configuration exposes the electrode only along one side of the vacuum coagulation probe and insulates the opposite side against transmission of radiofrequency energy and/or heat. As shown in FIGS. 1b, 1d and 1f, pores or holes 10 are created along one side of the electrode connecting the lumen 6 of the shaft 4 to the external surface of the electrode(s) 8. These pores 10 enable producing a vacuum against the soft tissue throughout the length of electrode(s) 8 thereby ensuring intimate tissue contact between the electrode(s) 8 and the soft tissue. The pores 10 also produce edges along the electrodes commonly associated with high current densities transmitted into the soft tissue. The combination of creating intimate tissue contact and directing the current density profile creates controlled and efficient heating of the soft tissue required when creating contiguous curvilinear, transmural lesions in atrial tissue (or other soft tissue). The pores may have a constant diameter or vary in diameter or profile along the length of the electrode to differ contact forces and/or current density profiles throughout the length of the electrode(s) 8.

The electrode(s) 8 may be fabricated from metal (e.g. tungsten, titanium, platinum, gold), metal alloy (e.g. stainless steel, spring steel, nickel titanium, etc.), metals deposited over a carrier (e.g. gold-plated stainless steel, gold deposited polyimide, platinum deposited polyester, etc.) or a combination of materials cut, with methods described previously, to define pores, shaft 4 attachment features (e.g. threads, slots, etc.) or other features. The electrode(s) may have a circular, elliptical, rectangular, curved, flattened, or other profile depending on tile function of the electrode(s). The electrode(s) may be fabricated from elastic or super-elastic materials so they can be deflected upon exposure to an external force (e.g. actuation of the vacuum, manual beading, etc.), or be treated so the electrode(s) is/are malleable so the operator may tailor the electrode(s) to the anatomic structures. Similarly, the shaft 4, described above, may be treated so it is malleable.

Figures 2A, 2B:
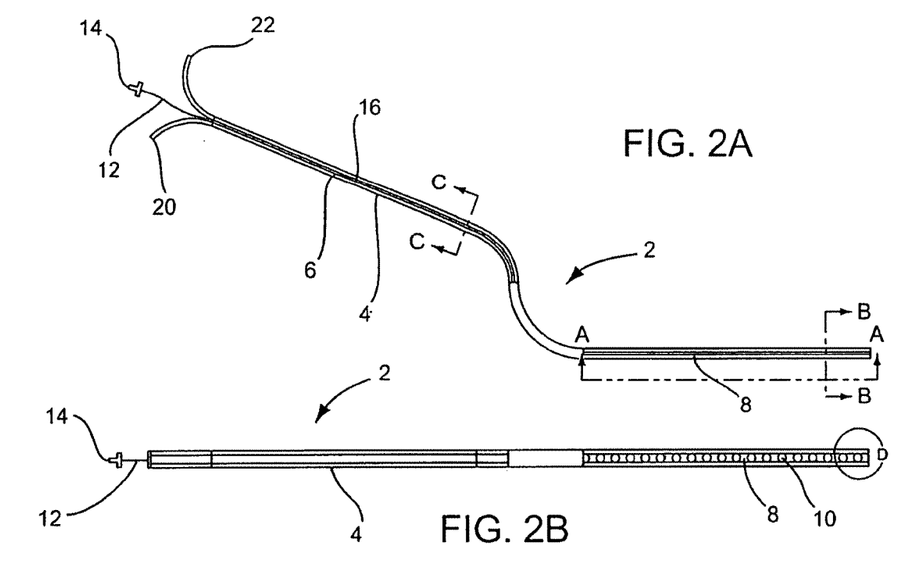
FIGS. 2a and 2b show a side view and a bottom view of a vacuum coagulation probe embodiment that incorporates tunneling/dissecting fluid injection capabilities.

FIGS. 2a and 2b show another vacuum coagulation probe embodiment used to coagulate soft tissue during minimally invasive access (e.g. thoracoscopic, endoscopic, arthroscopic, laparoscopic, or other approach) into the body cavity. A conventional cannulae, trocar or other postal is used to access the cavity though the skin and underlying tissues.

Figure 2C:
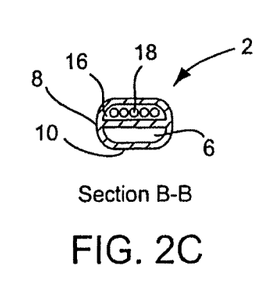
Figure 2D:
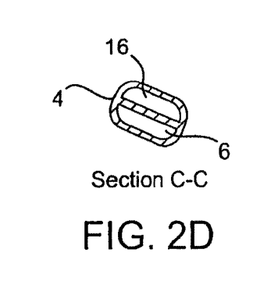
Figure 2E:
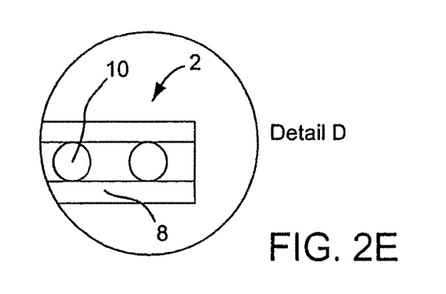
FIG. 2e shows a detailed view of region D taken from FIG. 2b.

The vacuum coagulation probe (2) embodiment in FIGS. 2a, 2b, 2c, 2d, and 2e incorporates a multi-lumen tubing shaft (4) that contains two lumens (6 and 16). The first lumen 6 links to pores (10) created in at least one electrode (8), as shown in FIG. 2c. The electrode embodiment in FIGS. 2a 2b, 2c, 2d, and 2e preferably consists of a length of sheet or bar material, having a predetermined wall thickness, secured to the multi-lumen shaft tubing along one side of the shaft. The electrode(s) may fit inside notches created in the shaft tubing that houses the electrode(s), adhesively bonded to an opening(s) in the shaft, ultrasonically welded to an opening(s) in the shaft, laser welded, spot welded or secured to the shaft with, another process depending on the materials used for the electrode(s), and the shaft. Alternatively, the electrode(s) may be fabricated from a multi-lumen tubing having the desired cross-section and secured to the shaft. For example, the multi-lumen electrode tubing may have the same cross-section profile as the shaft to maintain consistency in the lumen mating apposition. Another configuration involves fabricating the electrode(s) and the shaft from a single length of conductive tubing (e.g. single lumen or multi-lumen), or less conductive, tubing deposited or otherwise covered with a metallic coating. In these cases, the shaft region of the probe is covered with an insulative material to isolate the shaft from the electrode(s). In the embodiment shown in FIG. 2a, the shaft is preformed into an "S" configuration; alternatively, the shaft may be formed into any desired geometry depending on the access to the target coagulation location.

Figure 9:
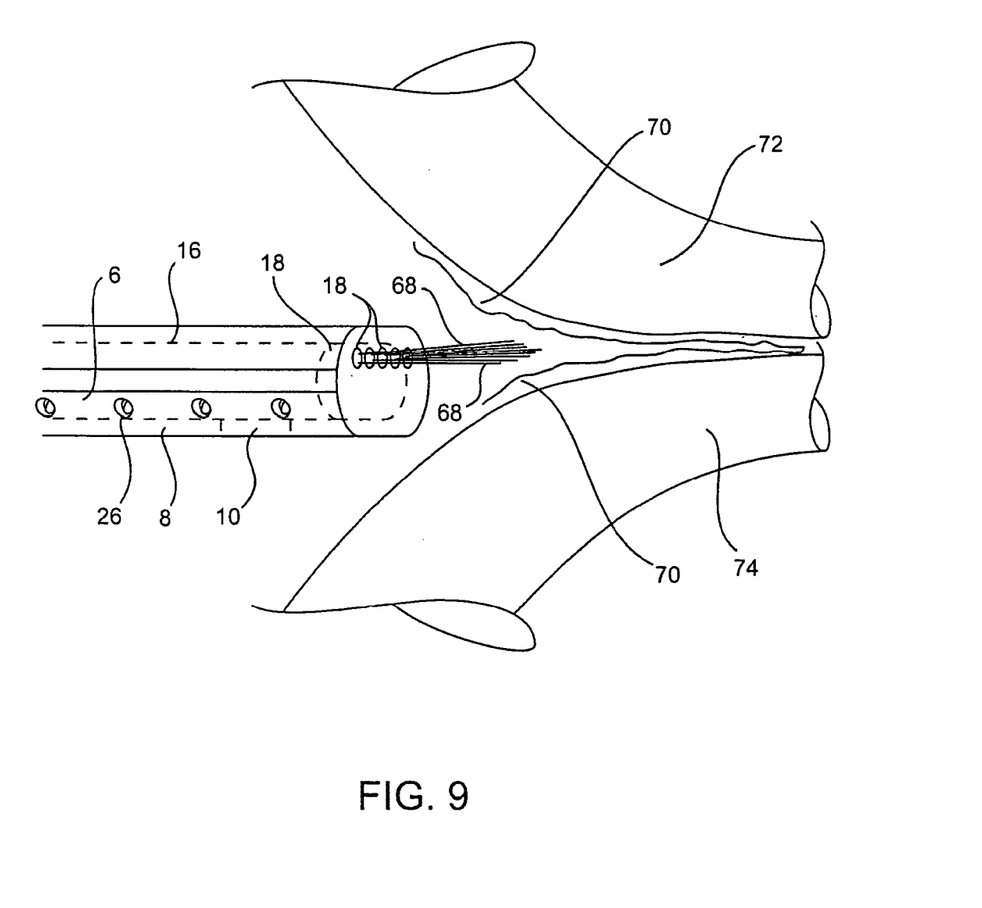
FIG. 9 shows a perspective view of a vacuum coagulation probe embodiment that incorporates a high intensity fluid injection system to tunnel between and/or dissect free anatomic structures.

As shown in FIGS. 2a, 2c, and 9, lumen 16 defined by the multi-lumen tubing routes a second port 22 at the handle to high velocity fluid injection pores 18 at the distal end of the vacuum coagulation probe 2 to enable separation and/or dissection of connective tissue, fatty deposits, or other tissue that covers target anatomic structures or holds the anatomy together. Injection of fluid through the high velocity fluid injection pores 18 produces high intensity streams (68) of fluid, as shown in FIG. 9, capable of disrupting certain connective tissues (70), fatty deposits, and other tissue without damaging vascular tissue (72 and 74), or other anatomic structures. As such, the vacuum coagulation probe is capable of tunneling through anatomic structures such as the pulmonary veins, the pulmonary artery, the aorta, or other anatomic structure to place the probe at any desired coagulation location and produce a clean surface of tissue for the probe to contact and improve the efficiency of coagulation by removing adventitia or other tissue. The fluid used to dissect and/or separate tissue may consist of saline, $CO_2$, air or other medium capable of being forced through the shaft 4 lumen 16 and past the distal end injection pores 18 to create high velocity streams. The injection pores 18 have a diameter between 0.0005" and 0.040" and are distributed throughout the distal end of the vacuum coagulation probe (or the sides) to direct the stream of injected high intensity fluid against the tissue to be dissected or separated. The pores may be angled such that the streams (68) intersect a distance away from the distal end of the probe to focus the dissection and/or tunneling force a specified distance from the distal end of the probe.

Figure 3:
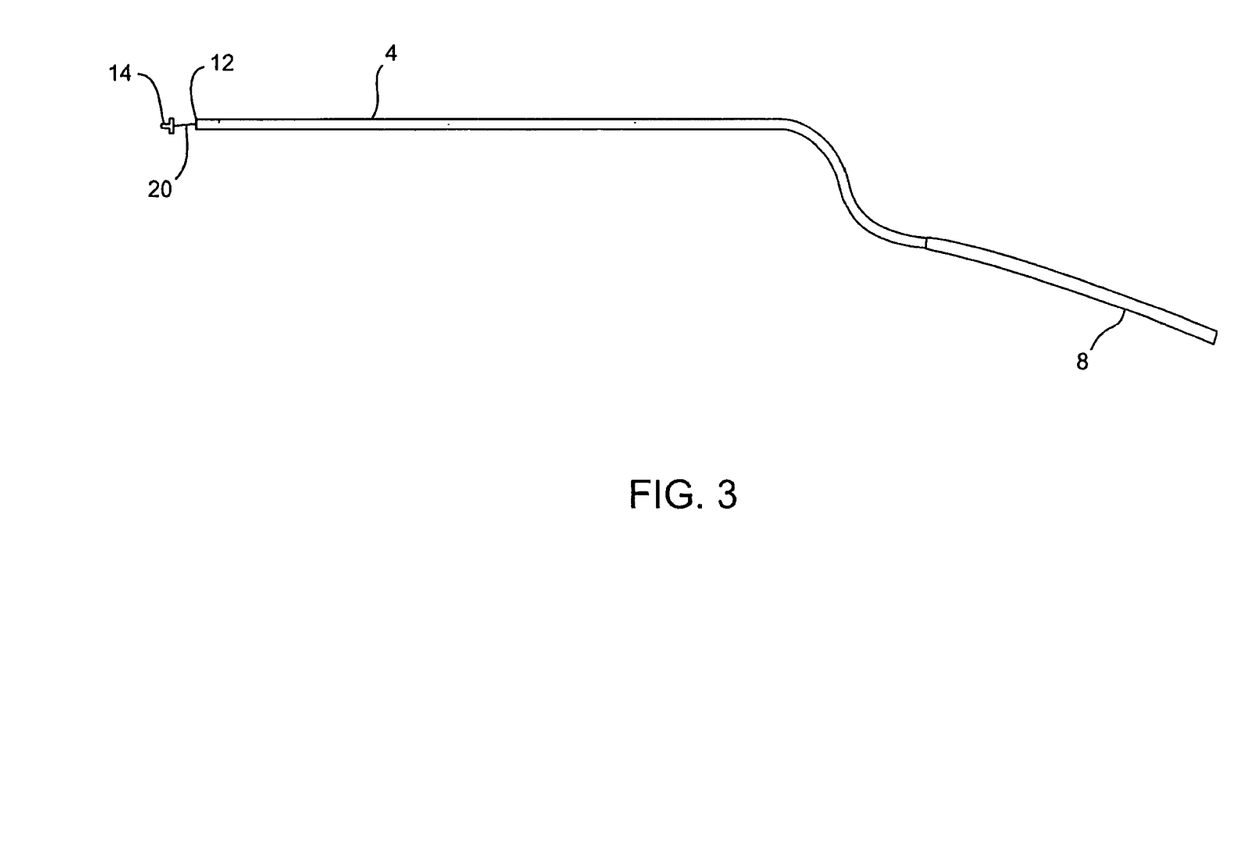
FIG. 3 shows a-side view of a vacuum coagulation probe embodiment deflected or bent to engage the soft tissue surface.

The embodiments described above may be treated so they are malleable and may be deformed into a desired shape, as shown in FIG. 3, required to access the desired coagulation location and/or create the desired lesion length, and shape. An alternative approach, not shown in the Figures, is to incorporate a steering mechanism in the vacuum coagulation probe. The steering mechanism may be used to deflect the entire electrode relative to the shaft and/or a portion of the electrode. At least one pull-wire can be secured to the electrode at the electrode to shaft junction if the electrode is to be deflected as a unit relative to the shaft, or along the electrode up to the distal end of the probe if the electrode is to be deflected. The opposite end of the pull-wire(s) are routed to the handle where it is secured to an actuation knob, not shown, to manually deflect the vacuum coagulation probe into a curve. The curve shape, angle and radius is defined by the distance along or from the electrode(s) at which the pull-wire(s) is/are secured and the stiffness relationship between the shaft and the electrode(s). A guide-coil or other radially restraining component can be housed around the pull-wire(s) in the shaft to specify the stiffness of the shaft and further define the radius of curvature and angle of deflection of the distal region of the probe as the pull-wires are actuated.

Figure 4A:
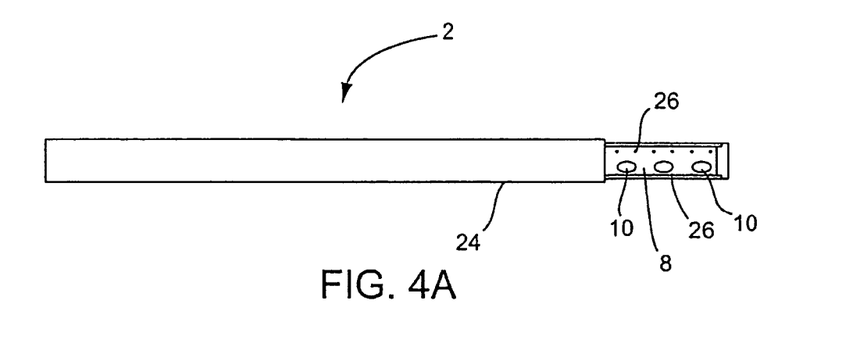
FIGS. 4a to 4c show side views of a vacuum coagulation probe embodiment that incorporates a movable insulation sheath to adjust the electrode length and convective cooling pores.
Figure 4B:
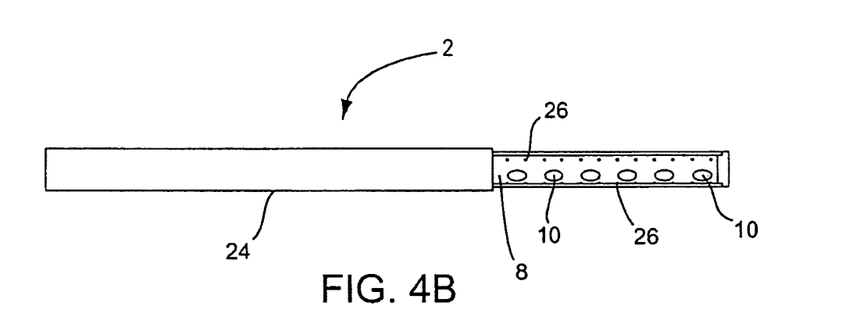
Figure 4C:
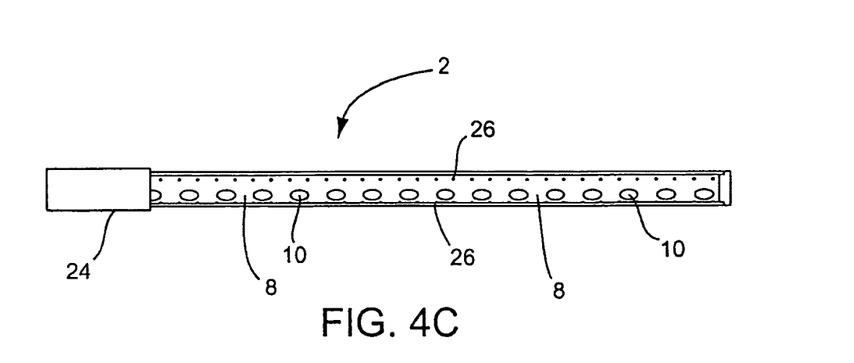

FIGS. 4a, 4b, and 4c show the distal section of another vacuum coagulation probe (2) embodiment. This probe (2) incorporates at least one electrode (8), one is shown in FIGS. 4a, 4b, and 4c, containing vacuum pores (10) defined as cuts though the at least one electrode (8). A moveable sheath 24 alters the length of the electrode(s) by insulating a proximal region of the electrode(s) from tissue and covering pores (10) in the proximal region of the electrode (8) such that tissue is not forced against the electrode(s) in the isolated region. FIG. 4a shows the probe (2) with the distal 15% of the electrode(s) exposed and used to vacuum contact and coagulate tissue. FIG. 4b shows the probe (2) with the sheath (24) retracted such that approximately 40% of the electrode(s) is/are exposed. FIG. 4c shows the probe (2) with the sheath further retracted such that approximately 85% of the electrode is/are exposed. The sheath (24) may be manipulated relative to the electrode(s) at any location to predetermine the length of the tissue to be coagulated into a lesion. The probe (2) embodiment in FIGS. 4a, 4b, and 4c further includes convective cooling pores (26) that may be connected to the vacuum lumen 6 such that actuation of the vacuum source not only causes the tissue to contact the electrode but produces a convective cooling of the tissue surface at the electrode-tissue interface capable of cooling the tissue surface and urging the maximum tissue temperature deeper into the tissue. Alternatively, the convective cooling pores (26) may be connected to the high velocity fluid injection lumen (16), or other conduit, such that saline, $CO_2$, air, or other medium may be injected through the electrode or adjacent the electrode to actively cool the electrode and/or the tissue surface immediately adjacent the electrode and urge the maximum tissue temperature deeper into tissue. The velocity of the fluid injected, the volume of injected fluid, and the temperature of the medium determines the amount of cooling and the magnitude of the effect upon tissue heating.

Existing atrial fibrillation coagulation or other soft tissue coagulation treatment applications performed thoracoscopically, endoscopically, arthroscopically, laparoscopically, or with other less invasive approach tend to create incomplete curvilinear lesions because the desired lesion sites are inaccessible, contact to the tissue is poor, and the temperature gradient from the contacted tissue surface to the opposite tissue surface is dramatic; these conditions limit the creation of contiguous, transmural, curvilinear, lesions. This is especially the case when blood is flowing along the opposite tissue surface producing a heat sink that cools that tissue surface further affecting the temperature gradient and limiting the lesion depth. As such, the existing techniques can be inferior and have a higher rate of arrhythmia persistence than the vacuum coagulation probe devices of the invention. In addition, incomplete lesions during atrial fibrillation treatment have been demonstrated to generate substrates for persistent atrial flutter and/or atrial tachycardia. For other applications, the inability to create consistent and complete lesions allows cancerous cells, or other disease substrates to prevail.

Figure 5:
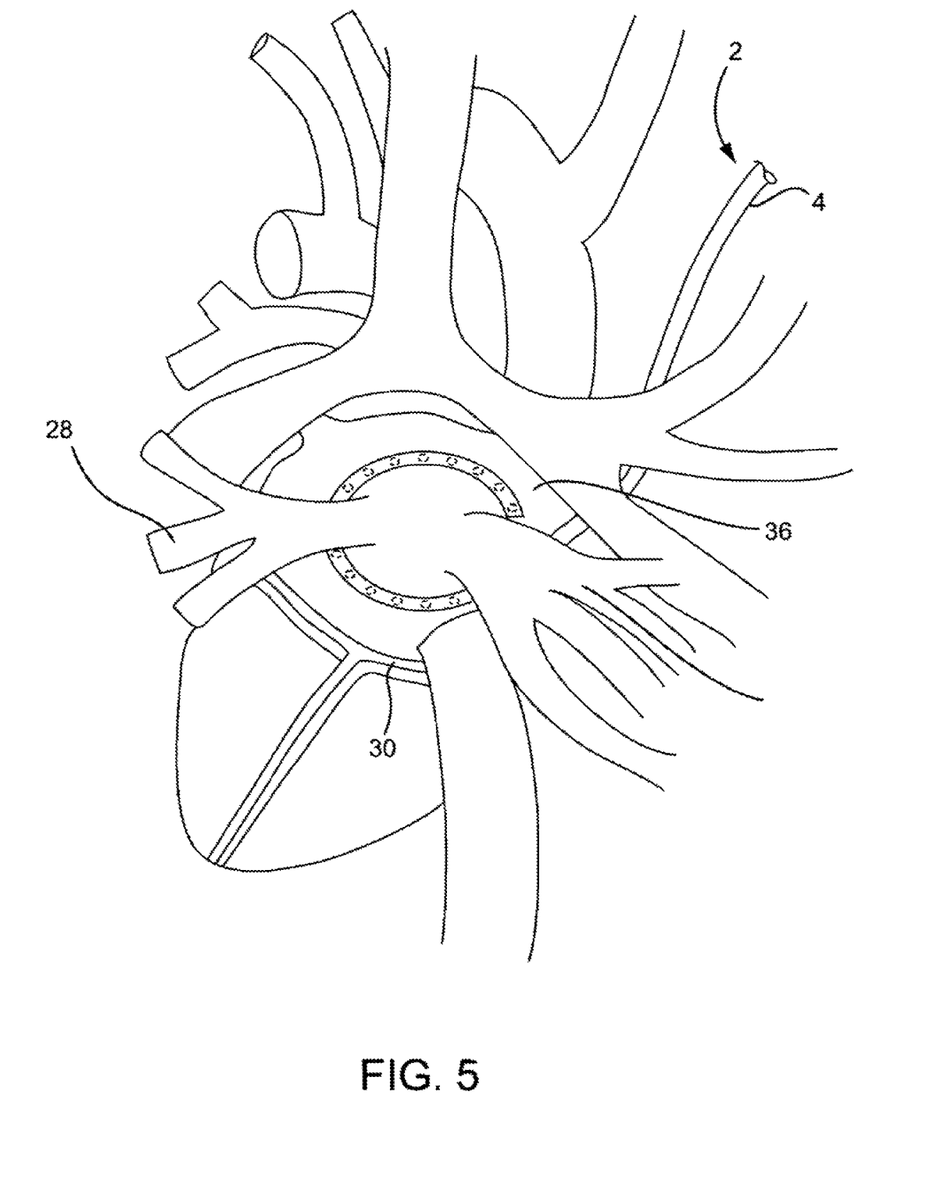
FIG. 5 shows a posterior view of the heart and associated vasculature with a vacuum coagulation probe embodiment accessing a desired lesion location along the left atrium.

An approach for treating atrial fibrillation with the vacuum coagulation probe (2) of the invention is shown in FIG. 5. The probe is inserted into the thoracic cavity though ports placed in intercostal spaces, a thoracotomy, a thoracostomy, a median sternotomy, a mini-sternotomy, xiphoid access port, a lateral subthoracic access site, or other less invasive surgical procedure. The probe (2) may contain high velocity fluid injection capabilities, as shown in FIGS. 2c and 9 and described above, to tunnel around or between vessels (72 and 74) such as the aorta, pulmonary artery, pulmonary veins (28), and/or other anatomic structures by separating and/or dissecting connective tissue (70), fatty deposits, and/or other tissue without damaging the vasculature (72 and 74). The probe (2) may be deflected or deformed into the desired lesion pattern, which in this case is circular or semi-circular passing around the right superior pulmonary vein, the right inferior pulmonary vein, the left inferior pulmonary vein, the left superior pulmonary vein, and terminating at the right superior pulmonary vein. Once placed, the vacuum source is actuated to apply a suction force through the vacuum pores (10) to urge the epicardium of the left atrium (36) into intimate contact with the electrode(s) (8). It should be noted that the vacuum coagulation probe can instead be placed against the endocardium of the atria during cardiopulmonary bypass procedures where the atria are open for valve (mitral, tricuspid, and/or atrioventricular) repair or replacement procedures or beating heat procedures where an introducer into the atrium is obtained through an atrial appendage, the atrial free wall, the ventricle, a pulmonary vein, a vena cava, or other conduit that may be closed upon completion of the coagulation procedure.

The entire length of the exposed electrode(s) is used to apply suction though the pores (10) to apply a vacuum force against the epicardium (or endocardium) and urge the tissue into engagement with the electrode(s). An insulative, movable sheath as shown in FIGS. 4a, 4b, and 4c may be used to alter the length of exposed electrode(s) and the target region of tissue that will be urged into engagement by the suction forces.

Then radiofrequency (or d.c.) energy is transmitted to the electrode(s) in unipolar or bipolar mode such that the current density is transmitted into tissue adjacent the electrode(s) and ohmic heating causes the tissue adjacent the electrode(s) to heat and conduct the heat further into the depths of tissue. Alternatively, the electrode(s) may be fabricated from a resistive element in which radiofrequency (or d.c.) energy applied along the resistive element, between wire connections at opposite ends of the resistive element, heats the element and the intimate tissue to electrode(s) contact enable thermal conduction of the heat into the target soft tissue.

The transmission of energy in unipolar or bipolar mode causes the soft tissue to heat which conducts further into adjacent soft tissue; alternatively the heating of a resistive element causes the resistive electrode(s) to heat which is then conducted into adjacent, contacted soft tissue. As cardiac cells (and any muscle tissue) is heated above 50° C., irreversible conduction block occurs and the cells become non-viable (Nath, et al. Cellular electrophysiologic effects of hyperthermia, on isolated guinea pig papillary muscle: implications for catheter ablation. *Circulation.* 1993; 88:1826-1831). As such, a consistent, continuous length of atrial tissue extending from the epicardial surface to the endocardial surface must be heated above 50° C. to treat atrial fibrillation.

For other applications involving coagulation of soft tissue to shrink collagen rich tissues or prevent shrinking of collagen tissues, heating of the soft tissue must be controlled, which the vacuum coagulation probe embodiments of the invention enable. Published studies evaluating the response of vessels (arteries and veins) to heat have focused on the ability to permanently occlude-vessels. Veins have been shown to shrink to a fraction of their baseline diameter, up to and including complete occlusion, at temperatures greater than 70° C. for 16 seconds; the contraction of arteries was significantly less than that of veins but arteries still contracted to approximately one half of their baseline diameter when exposed to 90° C. for 16 seconds (Gorisch et al. Heat induced contraction of blood vessels. *Lasers in Surgery and Medicine.* 2:1-13, 1982; Cragg et al. Endovascular diathermic vessel occlusion. *Radiology.* 144:303-308, 1982). Gorisch et al explained the observed vessel shrinkage response "as a radial compression of the vessel lumen due to a thermal shrinkage of circumferentially arranged collagen fiber bundles". These collagen fibrils were observed to denature, thus shrink, in response to heat causing the collagen fibrils to lose the cross-striation patterns and swell into an amorphous mass.

Embodiments of the invention prevent or limit the heat-induced contraction of such structures as the pulmonary veins by applying a vacuum force capable of maintaining the position (e.g. diameter) of the vessel while heating the soft tissue. As such, the vessel is stented or supported from the external surface as the tissue is heated above the required 50° C. threshold without concern that the vessel may accidentally become stenosed due to the heat-induced contraction.

Alternatively, the vacuum coagulation probe embodiments direct heat-induced contraction of such structures as tendons, skin or other anatomy in which the therapy is designed to heat thereby denature the collagen and shrink the tissue until the desired shape or effect is achieved. In addition, the vacuum coagulation probe can reposition the soft tissue while heat is applied to the soft tissue to direct the shrinking and cause the collagen fibrils to reorganize reforming the soft tissue into a desired shape.

Figure 6:
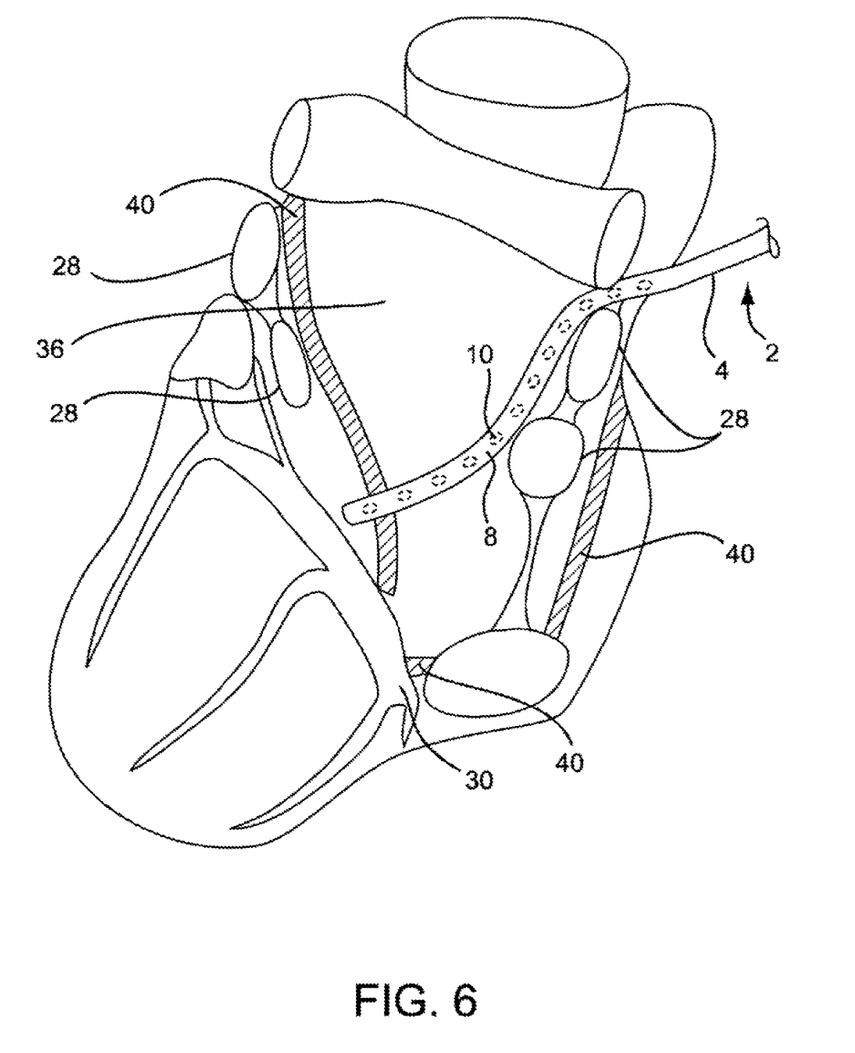
FIG. 6 shows a posterior view of the heart and associated vasculature with a vacuum coagulation probe embodiment used to create lesions along the left atrium and right atrium capable of treating atrial fibrillation.

FIG. 6 shows a posterior view of a heart with a vacuum coagulation probe embodiment placed between the right superior pulmonary vein 28 and the coronary sinus 30 to create a lesion extending from the right superior pulmonary vein to the right inferior pulmonary vein and finally ending at the coronary sinus. FIG. 6 shows this placement intersecting another lesion 40 previously created with the vacuum coagulation probe embodiment and extending from the left superior pulmonary vein to the left inferior pulmonary vein and ending at the coronary sinus. FIG. 6 also shows light atrial lesions created with the vacuum coagulation probe extending from the superior vena cava to the inferior vena cava, and from the inferior vena cava to the tricuspid valve annulus located along the atrial-ventricular groove proximate the coronary sinus orifice. Such lesion patterns described above have been demonstrated to terminate atrial fibrillation provided they are contiguous, transmural, and extend to the barriers (e.g. the branching vessels, atrio-ventricular groove, or other structure that inhibits electrical propagation).

Figure 7A:
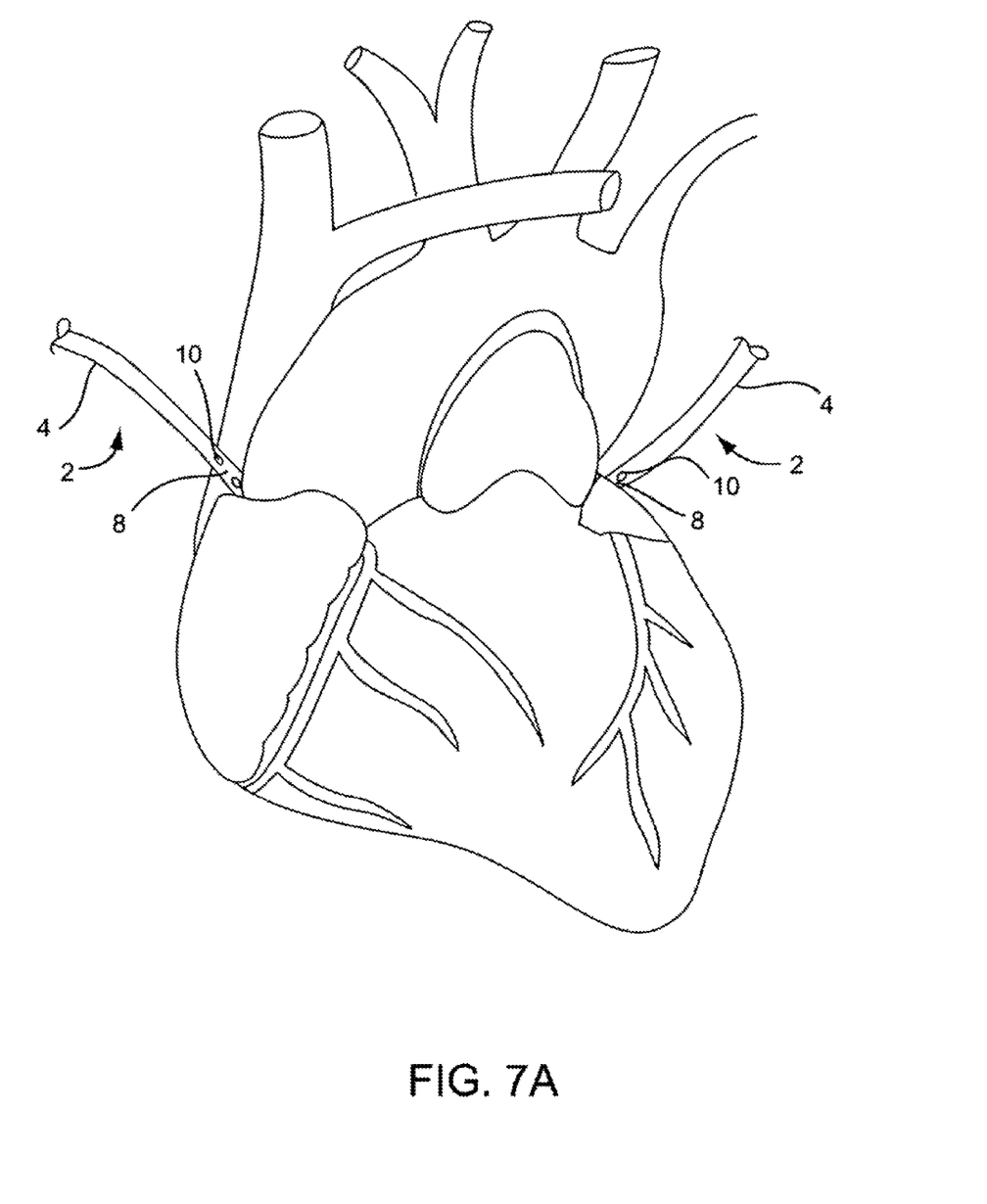
FIG. 7a shows an anterior view of a heart and associated vasculature with a vacuum coagulation probe embodiment placed to access regions of the left atrium about the pulmonary veins.
Figure 7B:
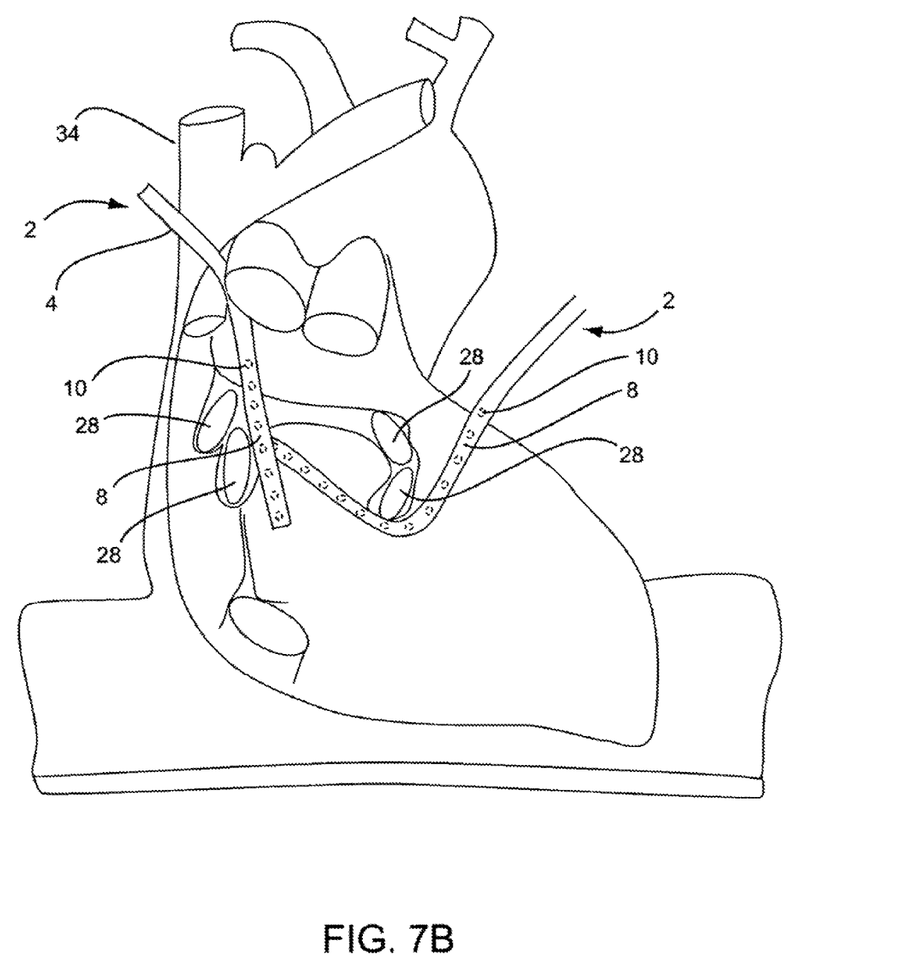
FIG. 7b shows a region of the thoracic cavity with the heart removed, but associated vasculature in place, to show access sites along the left atrium for a vacuum coagulation probe embodiment to create lesions capable of treating atrial fibrillation.

FIGS. 7a and 7b show an anterior view of a heart and a cut away view with the heart removed having two vacuum coagulation probes 2 advanced between vascular structures to access the posterior region of the left atrium about the pulmonary veins. As FIGS. 7a and 7b show, a first vacuum coagulation probe accessing the heart from the anterior surface of the thoracic cavity between the aorta and the superior vena cava, adjacent the right superior pulmonary vein, past the right inferior pulmonary vein, and down to the atria-ventricular groove; the electrode(s) (8) create a lesion from the atria-ventricular groove along the right pulmonary veins. The second vacuum coagulation probe enters the thoracic cavity and extends around the left ventricle of the heart, passes around the left inferior pulmonary vein, and intersects the first vacuum coagulation probe. The electrode(s) for this probe extend along the left atrium around the left inferior pulmonary vein and terminates at or past the lesion created with the first probe. It should be noted that any pattern of curvilinear, transmural lesions may be created along the epicardial surface or the endocardial surface with the vacuum coagulation probe embodiments of the invention. Other potential lesion patterns capable of treating atrial fibrillation, which the vacuum coagulation probe may replicate, are described in U.S. Pat. No. 6,071,279 entitled "Branched structures for supporting multiple electrode elements" and incorporated herein by reference.

Figure 8A:
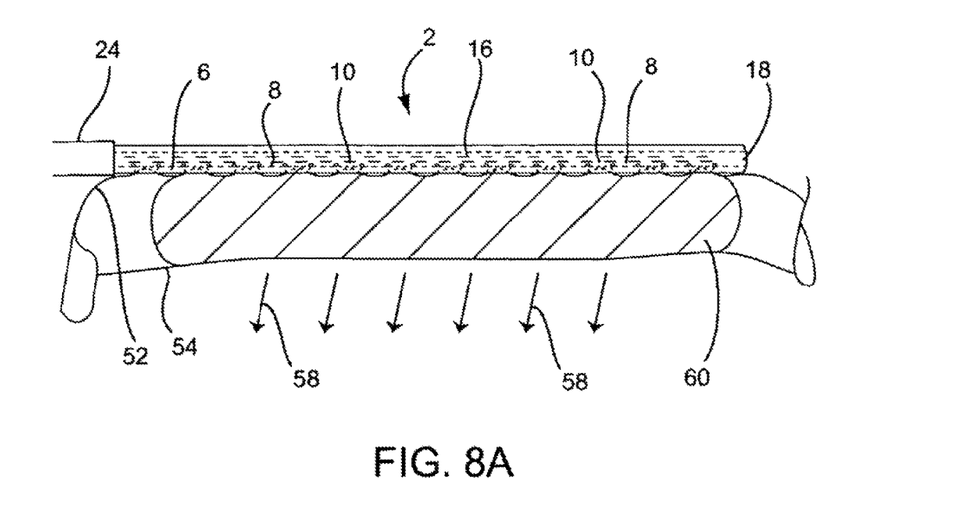
FIG. 8a shows a side-sectional view of a vacuum coagulation probe embodiment with the vacuum pores actuated to ensure intimate and complete contact between a tissue surface and the probe electrode.
Figure 8B:
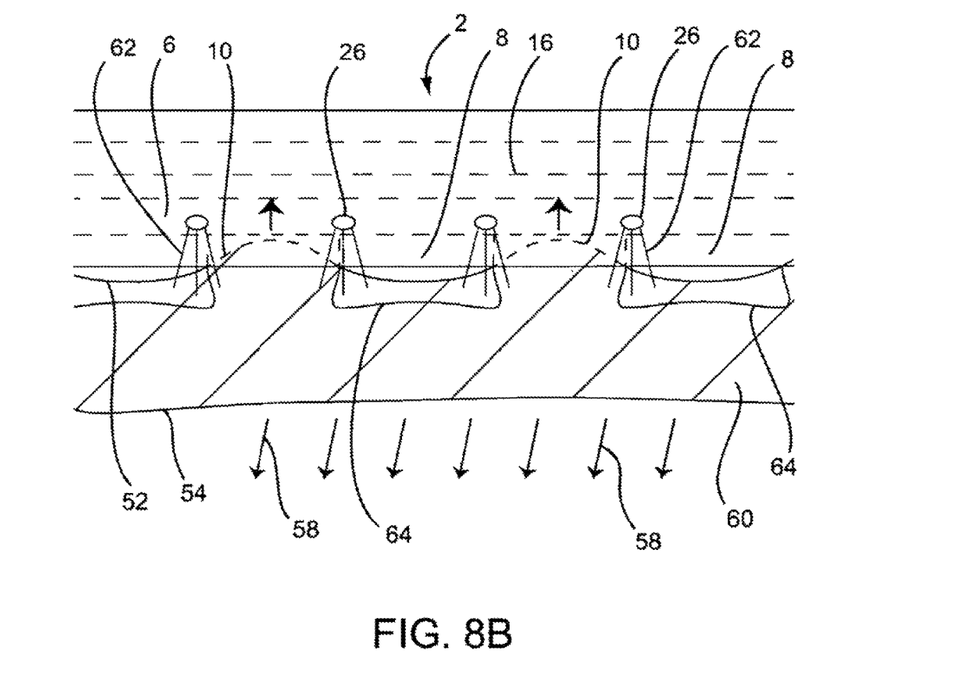
FIG. 8b shows a close-up side-sectional view of the vacuum coagulation probe embodiment in FIG. 8a with the vacuum pores actuated to urge soft tissue into intimate contact with the electrode, coagulation energy transmitted through the electrode into tissue to create a curvilinear, transmural lesion, and convective cooling pores to decrease the surface temperature of the soft tissue and urge the maximum temperature deeper.

FIGS. 8a and 8b show a side view and a close-up view of the vacuum coagulation probe in FIGS. 4a, 4b, and 4c with the suction actuated to urge the epicardium (52) (or endocardium) into engagement with the electrode(s) (8) about the vacuum pores (10). A contiguous transmural lesion extending from the epicardium (52) to the endocardium (54) is created spanning the length of the exposed electrode(s). A sheath (24) masks a proximal region of electrode(s) and associated vacuum pores to limit the lesion to a desired length. Radiofrequency (or d.c.) energy is transmitted to the electrode(s) and into the contacted tissue. The current density pattern (64) has the highest values adjacent the edges of the pores (10) because these edges represent a dramatic transition from a conductive material to an insulative (or less conductive) region producing edge effects that result in high current density profiles. As shown in FIG. 8b, convective cooling pores (26) connected through the vacuum lumen (6) or the injection lumen (16) can be placed along the lateral sides of the electrode(s) (8) to utilize suction of air or fluid or injection of cooled saline, $CO_2$, air or other media to produce a surface cooling of the epicardium and urge the maximum temperature deeper into the soft tissue. The suction force used to produce intimate contact between the epicardial surface and the electrode(s) helps counteract the effects of endocardial convective cooling caused by blood flowing 58 along the endocardial surface taking heat away and cooling the tissue adjacent the endocardium. The suction force compresses the tissue against the electrode(s) decreasing the depth of tissue (60) through which thermal conduction must extend. Suction also makes energy delivery more efficient by optimizing tissue contact throughout the length of the electrode(s) such that regions of the electrode(s) not in intimate tissue contact do not hinder energy transmission for those regions that are in intimate contact, as is the case with conventional approaches. The incorporation of convective cooling pores (26) along the sides of the electrodes further affects the temperature gradient by utilizing a vacuum source or an injection source to flow a fluid medium (air, $CO_2$, saline, etc.) (62) along the epicardial surface actively cooling the surface and allowing more energy to be transmitted into the soft tissue which correspondingly heats more tissue and urges the maximum tissue temperature deeper.

The embodiments of the invention described in this specification can also be used for coagulating other soft tissues such as breast tissue, the liver, the prostate, gastrointestinal tissue, skin, or other soft tissue for the coagulation of cancerous cells; or tendons, or other collagen based soft tissue for the heat induced shirking or contraction.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims of the invention.

The invention claimed is:

1. A method for coagulating a soft tissue comprising:
   placing an elongate member against the soft tissue, the elongate member comprising at least one vacuum lumen and at least one element, where the at least one element is in fluid communication with the vacuum lumen wherein said elongate member further comprises a non-conductive sheath covering a length of said at least one element and movable relative to said at least one element, and advancing or retracting said non-conductive sheath relative to said element until an exposed length of said element equals a desired lesion length before or after advancing said element against said soft tissue surface;
   applying a vacuum source to produce a vacuum in said lumen such that the vacuum passes through the at least one element to draw tissue in contact with a length of the at least one element; and
   transmitting energy through the at least one element to create a contiguous lesion in the soft tissue where the contiguous lesion has a length that corresponds to the length of the at least one element that contacts the tissue.

2. The method of claim 1, wherein said elongate member is malleable and the step of placing said elongate member against the length of soft tissue comprises deforming said elongate member and said element before or after advancing said element against said soft tissue surface.

3. The method of claim 1, wherein said elongate member further comprises at least one fluid injection opening and said step of placing said elongate member against soft tissue surface comprises tunneling between or dissecting around anatomic structures to expose said soft tissue surface before advancing said conductive element against said soft tissue surface.

4. The method of claim 1, wherein said step of placing said elongate member against the length of soft tissue comprises tunneling or dissecting around pulmonary veins to engage said element against a left atrial surface associated with the pulmonary veins.

5. The method of claim 1, where the element comprises a bipolar element.

6. The method of claim 1, where the element comprises a unipolar element.

7. A method for coagulating a length of soft tissue comprising:
   placing an elongate member against a surface of the soft tissue, the elongate member comprising at least one lumen, at least one element, and at least one opening through said element where the opening is fluidly coupled to said lumen wherein said elongate member further comprises a non-conductive sheath covering a length of said element and movable relative to said element, and advancing or retracting said non-conductive sheath relative to said element until an exposed length of said element equals a desired lesion length before or after advancing said element against said soft tissue surface;
   applying a vacuum source to produce a vacuum in said lumen and through said opening to cause said soft tissue to contact a length of said element at said opening; and
   transmitting energy through said element to heat said soft tissue wherein said step of heating said soft tissue comprises coagulating a contiguous lesion in the soft tissue by applying energy to said element contacting the soft tissue where a length of the contiguous lesion corresponds to the length of the at least one element that contacts the soft tissue.

8. The method of claim 7, wherein at least one of said elongate member and said element are malleable such that upon exposure to an external force the element deforms against said soft tissue surface and where suction from the vacuum source is applied to an entire exposed length of the element in the entire length of the opening allowing coagulation of the soft tissue surface along the entire length of the opening.

9. The method of claim 7, wherein said elongate member further comprises at least one fluid injection opening and said step of placing said elongate member against soft tissue surface comprises tunneling between or dissecting around anatomic structures to expose said soft tissue surface before advancing said conductive element against said soft tissue surface.

10. The method of claim 7, wherein said step of placing said elongate member against a soft tissue surface comprises tunneling or dissecting around pulmonary veins to engage said element against a left atrial surface associated with the pulmonary veins.

11. A method for coagulating a length of sort tissue comprising:
   placing an elongate member against the length of soft tissue, the elongate member comprising at least one vacuum lumen and at least one element configured to coagulate tissue, where the at least one element is in fluid communication with the vacuum lumen;
   applying a vacuum source to said lumen such that the vacuum source draws tissue in contact with the at least one element;
   transmitting radiofrequency energy through the at least one element to create a contiguous, transmural lesion in the soft tissue by transmitting radiofrequency energy through into the contacting the length of soft tissue; and where
   said elongate member further comprises a non-conductive sheath covering a length of said elongate member and movable relative to said elongate member, and the step of placing said elongate member against the length of soft tissue comprises advancing or retracting said sheath relative to said member until the length of exposed element equals the desired lesion length before or after advancing said element against said soft tissue surface.

* * * * *